United States Patent
Doken et al.

(10) Patent No.: US 12,360,716 B2
(45) Date of Patent: Jul. 15, 2025

(54) METHODS AND SYSTEM FOR ALLEVIATING NECK PAIN DURING MEDIA CONSUMPTION

(71) Applicant: Adeia Guides Inc., San Jose, CA (US)

(72) Inventors: Serhad Doken, Bryn Mawr, PA (US); Ning Xu, Irvine, CA (US); Jean-Yves Couleaud, Mission Viejo, CA (US); Reda Harb, Tampa, FL (US)

(73) Assignee: Adeia Guides Inc., San Jose, CA (US)

( * ) Notice: Subject to any disclaimer, the term of this patent is extended or adjusted under 35 U.S.C. 154(b) by 0 days.

(21) Appl. No.: 18/375,118

(22) Filed: Sep. 29, 2023

(65) Prior Publication Data

US 2025/0110677 A1     Apr. 3, 2025

(51) Int. Cl.
*G06V 20/59*     (2022.01)
*A61B 5/11*      (2006.01)
(Continued)

(52) U.S. Cl.
CPC .......... *G06F 3/14* (2013.01); *G06T 7/20* (2013.01); *G06T 7/70* (2017.01); *G06V 20/59* (2022.01); *A61B 5/1116* (2013.01); *A61B 5/165* (2013.01); *A61H 2230/62* (2013.01); *A61H 2230/625* (2013.01); *A61N 1/36535* (2013.01); *A63B 23/0244* (2013.01); *B60W 2540/223* (2020.02);
(Continued)

(58) Field of Classification Search
CPC ..... G06F 3/14; G06T 7/20; G06T 7/70; G06T 2207/30196; G06V 20/59; G06V 20/597; G06V 40/175; G06V 40/176; A61B 5/1116; A61B 5/165; A61H 2230/62; A61H 2230/625; A61N 1/36535; A63B 23/0244; B60W 2540/223; G08B 21/0446
See application file for complete search history.

(56) References Cited

U.S. PATENT DOCUMENTS

2022/0203996 A1* 6/2022 Katz .................. B60W 50/14
2022/0282826 A1* 9/2022 Hong .................. F16M 11/10

FOREIGN PATENT DOCUMENTS

JP        2023016215 A  *  2/2023

OTHER PUBLICATIONS

Health Matters NYP, "How to Prevent 'Tech Neck," (https://healthmatters.nyp.org/how-to-prevent-tech-neck/)(5 pages).
(Continued)

*Primary Examiner* — Douglas Wilson
(74) *Attorney, Agent, or Firm* — Haley Guiliano LLP

(57) ABSTRACT

Systems and methods for alleviating neck pain during media consumption. The methods and systems comprise determining, using control circuitry a current orientation of each of a user's head and a user device, determining an environmental parameter relating to the user's environment, determining a range of permitted orientations of the user's head based on the environmental parameter and the current orientations of the user's head and the user device, determining, using control circuitry, whether the orientation of the user's head is outside of the range of permitted orientations, and in response to determining that the orientation of the user's head is outside of a range of permitted orientations, causing, using control circuitry, a change in a mode of display of the user device.

18 Claims, 11 Drawing Sheets

(51) Int. Cl.
*A61B 5/16* (2006.01)
*A61N 1/365* (2006.01)
*A63B 23/02* (2006.01)
*G06F 3/14* (2006.01)
*G06T 7/20* (2017.01)
*G06T 7/70* (2017.01)
*G06V 40/16* (2022.01)
*G08B 21/04* (2006.01)

(52) U.S. Cl.
CPC .. *G06T 2207/30196* (2013.01); *G06V 20/597* (2022.01); *G06V 40/175* (2022.01); *G06V 40/176* (2022.01); *G08B 21/0446* (2013.01)

(56) References Cited

OTHER PUBLICATIONS

Kohei Arai, et al., "Head Position and Pose Model and Method for Head Pose Angle Estimation based on Convolution Neural Network," (https://thesai.org/Downloads/Volume12No10/Paper_6-Head_Position_and_Pose_Model_and_Method.pdf)(8 pgs).

Lacanlale, et al. "Sensoring the Neck: Classifying Movements and Actions with a Neck-Mounted Wearable Device," (https://doi.org/10.3390/s22124313)(14 pages).

Lee S, Kang H, Shin G., "Head flexion angle while using a smartphone," (Ergonomics. 2015);(Epub Oct. 17, 2014) (https://pubmed.ncbi.nlm.nih.gov/25323467/), (2 pages).

Lindsay Mack, "The Top 5 Apps That Help You Improve Your Posture," (https://www.makeuseof.com/apps-to-improve-posture/)(Published Apr. 7, 2022)(8 pages).

M Ramnaath et al., "Muscle Fatigue and Head Flexion Angle Analysis while using Smartphone," (2020 IOP Conf. Ser.: Mater. Sci. Eng. 912 062017)(https://iopscience.iop.org/article/10.1088/1757-899X/912/6/062017/pdf)(14 pages).

Marlynn Wei M.D., "5 Ways Stress Hurts Your Body, and What to Do About It," (https://www.psychologytoday.com/us/blog/urban-survival/201505/5-ways-stress-hurts-your-body-and-what-do-about-it)(Psychology Today)(4 pages).

* cited by examiner

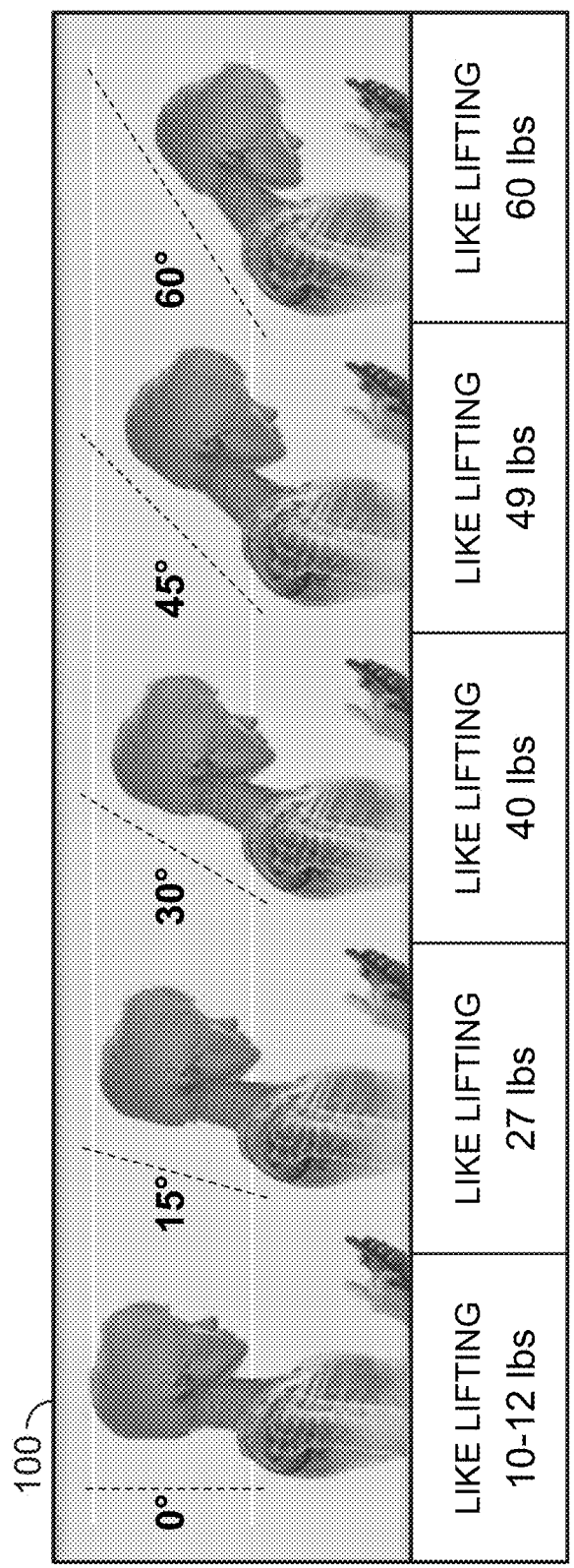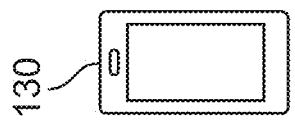
FIG. 1

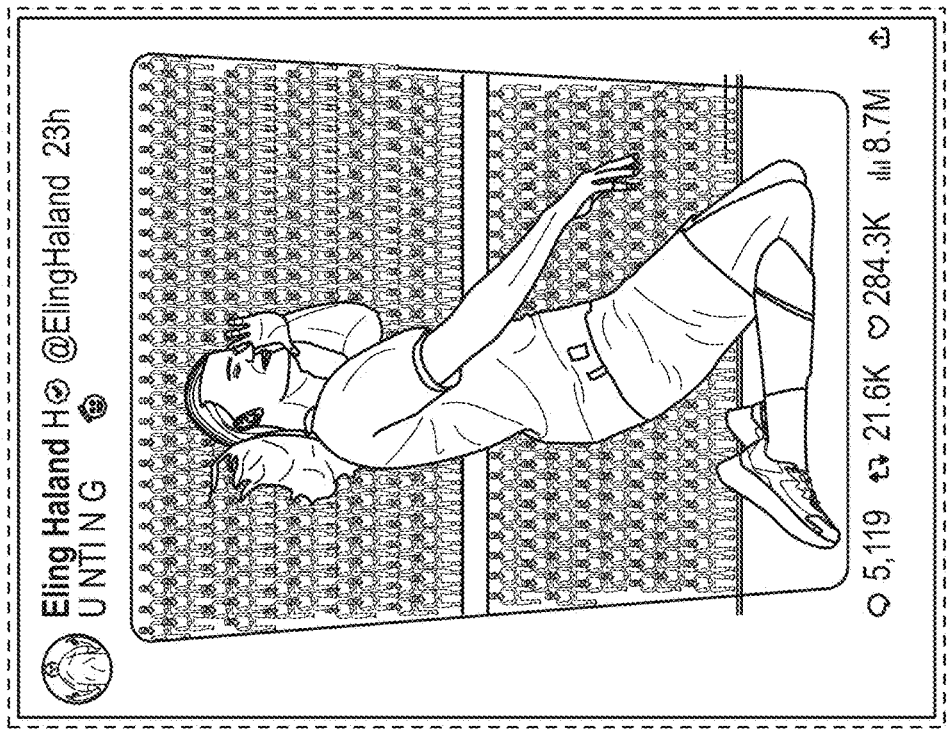
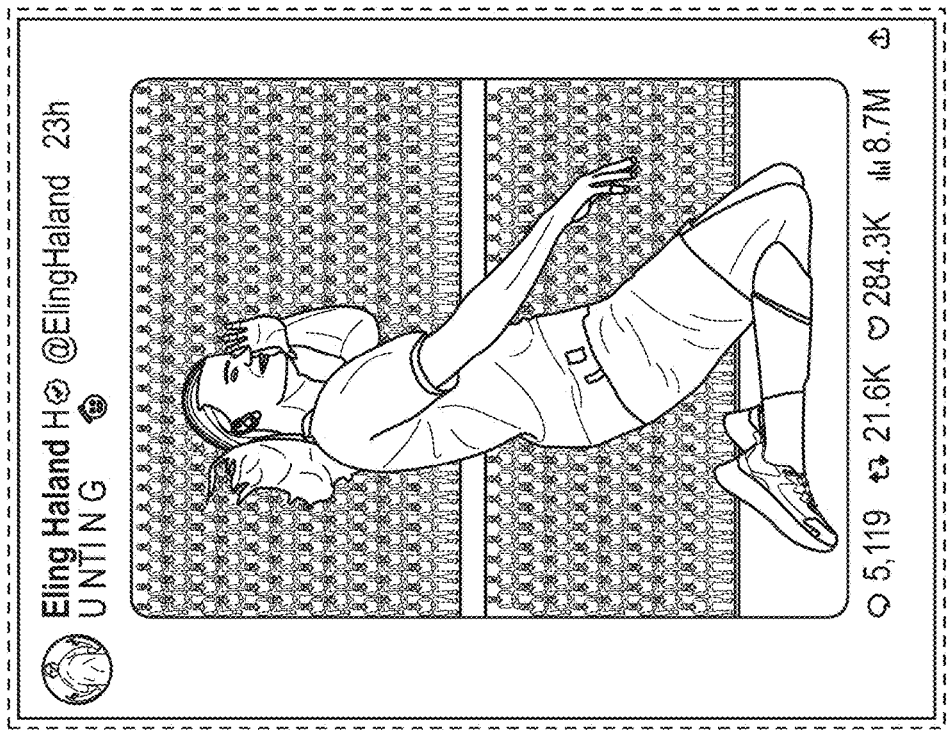
FIG. 2

METHODS AND SYSTEM FOR ALLEVIATING NECK PAIN DURING MEDIA CONSUMPTION

FIELD

The present disclosure relates to methods and systems for alleviating neck pain during media consumption, and more particularly, to methods and systems for causing a change in a display device or user device to aid a user in alleviating neck pain or keeping a user's gaze away from a user device.

BACKGROUND

In contemporary society, individuals have developed a pronounced reliance on their mobile electronic devices, particularly smartphones and tablets. Their engagement with these personal gadgets far surpasses the time dedicated to traditional media devices, such as television. Frequently, people become so engrossed in the applications on their devices that they disregard their immediate surroundings while walking, putting themselves at risk of colliding with others. These devices exert an incessant pull on their attention, leading individuals to scrutinize their screens at progressively closer proximities, often contorting their necks in the process. As of 2023, statistics indicated that Americans allocated an average of 4 hours and 25 minutes per day to non-voice activities on mobile devices. In addition, 6% of Americans check their phone within the first 10 minutes of waking up. Moreover, 27.1% admit to using and/or looking at their phone while driving.

"Text neck" refers to a repetitive stress injury or overuse syndrome affecting the cervical region of the neck, which arises from prolonged usage of mobile devices that necessitates a downward bent position of the head with minimal movement. This condition, alternatively referred to as "tech neck," is most commonly associated with texting activities; however, it can be attributed to a range of tasks executed on smartphones and tablets that require a downward gaze, including but not limited to browsing social media, engaging in gaming, or viewing videos. Typical symptoms encompass headaches, neck stiffness, spasms in the neck musculature, and discomfort between the shoulder blades. Individuals afflicted with text neck may encounter difficulty in resuming an upright head posture after extended periods of looking downward. In more severe instances, this condition can lead to sensations of numbness, tingling, or weakness radiating down the arms, resulting from impingement of a nerve in the cervical region. The initial mechanism involves muscular strain as the muscles labor to support the head's weight in an elevated position. However, prolonged strain leads to muscle tightening, which subsequently increases pressure on the intervertebral discs. This heightened pressure accelerates disc wear and tear, potentially resulting in disc bulging or rupture. In cases where a ruptured disc compresses a nerve, it can elicit pain, weakness, or numbness in the affected arm, potentially necessitating surgical intervention for resolution.

The human head can weight anywhere between 5 and 11 pounds, a seemingly modest figure; nonetheless, this mass exerts a notable burden on the cervical region. Even in instances of impeccable posture maintenance and an upright head position, the spinal column is inevitably subjected to a force equivalent to the weight of the head, ranging from 5 to 11 pounds, due to the force of gravity. However, once the head undergoes forward flexion, the biomechanical stresses imposed upon the spinal column extend beyond the static gravitational influence and escalate further due to, for example, moment arms. A moment arm is the length between a joint axis and the line of force acting on that joint; there is a paucity of data available for the moment arms of the muscles of the human neck. For example, as the forward flexion of the human head occurs, the moment arm of the neck increases, increasing the torque in the neck joints up to a equivalent force of 60 pounds, without any external movement forces.

SUMMARY

This disclosure is to devise a method for continuously assessing the angle of head tilt in relation to the screen of a mobile device, including phones and tablets, and to provide users with occasional prompts, which may be either implicit or explicit, whenever predefined health-related thresholds are exceeded. While existing applications have been developed to address this concern, they predominantly lack the capability to monitor the user's real-time activity or discern patterns of user engagement, particularly in the context of media consumption and interaction. These existing applications often resemble post-facto physical therapy exercises, as opposed to actively influencing and guiding user behavior during their device usage.

In a first approach, there is provided a method comprising determining, using control circuitry a current orientation of each of a user's head and a user device; determining an environmental parameter relating to the user's environment; determining a range of permitted orientations of the user's head based on the environmental parameter and the current orientations of the user's head and the user device; determining, using control circuitry, whether the orientation of the user's head is outside of the range of permitted orientations; and in response to determining that the orientation of the user's head is outside of a range of permitted orientations, causing, using control circuitry, a change in a mode of display of the user device.

In some examples, in response to determining that the orientation of the user's head is outside of a range of permitted orientations, the method alternatively or in addition comprises outputting, using control circuitry, a cautionary notification to the user device. In some examples, the cautionary notification is audio and/or haptic feedback indicative of the user's head being outside the range of permitted orientations.

For example, a user device determines a current orientation of each of a user's head and user device, e.g., by using the camera of the user device, internal gyroscopes and accelerometers, proximity and ambient sensors of the user device. Environmental parameters or contextual factors relating to the user's environment, such as whether the user is standing, sitting, lying down or in a car, are determined. The range for the permitted orientations of the user's head is determined, which is based on the environmental parameters or contextual factors, for example, the permitted range for a user lying down is different to that of a user driving. It is determined whether the orientation of the user's head is outside of the permitted range, which is an indication that the user is at risk of neck strain or looking away from the road while driving. In response to the determination that the user's head is outside of the range of permitted orientation, a change in mode of display of the user device such as issuing a notification; changing a pitch, angle or yaw of the displayed content; transferring the displayed content to another screen (i.e., handing off the displayed content to another user device); disabling the display for a time period; or the like.

In some examples, in response to the determination that the user's head is outside of the range of permitted orientation, a change mode of display may comprise deactivating the display, e.g., in combination with another measure such as maintaining audio. In this way, when the display is disabled, it serves as a prompt for the user to correct their posture. For instance, if the user is hunched over or looking down at their device, disabling the display encourages them to raise their head and align their neck with a more ergonomic posture. In some examples, a change in a mode of display comprises deactivating (or at least reducing a level of output of) a display screen, while continuing an audio output. For example, an audio output may be an uninterrupted continuation of an audio output related to a media content item that was being displayed prior to deactivation of the screen. Additionally or alternatively, an audio output may relate to a notification regarding the deactivation of the display. In the context of the present invention, "deactivation" of a display refers to turning a display off, or ceasing to display a media content item on the display. In some examples, an audio output may be provided on one or more external systems associated with the display, such as a vehicle system paired with the display. Moreover, in some examples, the system can offer customizable feedback to the user when the display is disabled, with audio. This feedback can include educational information about proper posture, tips for ergonomics, and recommendations for stretches or exercises to alleviate discomfort and maintain healthy posture. In addition, in some examples, over time, the system can adapt and become more effective in prompting posture corrections based on user behavior and preferences. The system can refine its feedback and interruption strategies to align with individual needs.

In some examples, the method comprises determining a proximity of the user device to the user's head, wherein determining the range of permitted orientations is further based on the proximity of the user device to the user's head.

For example, taking some data about the user's proximity to the device and their head size during a calibration step, enables the use of trigonometry to determine the user's head tilt angle, $T_N$, as the arccosine of the proximity of the user, $Prox_N$, over the users head size, HeadSize:

$$T_N = \text{Cosine}^{-1}\left(\frac{Prox_N}{HeadSize}\right)$$

In some examples, determining the environmental parameter relating to the user's environment comprises: determining a motion of a frame of reference of the user relative to a motion of the user device. In this way, the system and methods can take into account the additional strain owing to, for example, the motion of a vehicle.

In some examples, the method comprises determining the orientation of a user's head using a driver monitoring system/occupant monitoring system (DMS/OMS) of a vehicle. In some examples, the DMS/OMS monitors all occupants of a vehicle. In some examples, the method comprises determining a level of user interaction with the user device; and receiving, at the user device, an instruction from the driver monitoring system restricting operation of the user device when the level of user interaction is greater than an interaction value.

In some examples, the method further comprises enabling a continuation of the level of user interaction using a vehicle system (e.g., a handover from the user device to a car display device(s) or a particular display device in the car such as displays in rear of the vehicle, and continuing the user's application use on the car display device, such as music, news, contacts, maps, and the like). In some examples, the method further comprises determining a level of autonomy of the vehicle, wherein the interaction value is based on the level of autonomy (e.g., autonomous driving level of the vehicle permits user to do more with their phone/level of notifications decreases/increasing time limits, that is to say the permitted range).

In some examples, the method comprises determining a physiological parameter of the user; estimating a level of tension of the user based on the physiological parameter; wherein determining the range of permitted orientations is further based on the estimated level of tension.

For example, a physiological parameter, such as the user's heart rate, blood pressure, oxygen saturation level, decrease in blood flow, lactic acid build-up, and the accumulation of toxic metabolites, can be determine and used to estimate a level of tension of the user based on one or more of these parameters. Tension can be an indication of physical tension or of the user's state of mind, which can be further used to refine the range of permitted orientations of the user device; if an increase in tension is determined, a smaller range of movement will be permitted to reduce further tension on the user's neck.

In some examples, the method comprises determining a change in a position of a facial landmark of the user; estimating a level of tension of the user based on the change in a position of a facial landmark of the user; wherein determining the range of permitted orientations is further based on the estimated level of tension.

For example, a muscle twitch, fidgeting, stretching, yawning, blinking, squinting, or the like may be understood to be examples of a change in position of a facial landmark of the user. Therefore, tension of the user can be estimated based on one or more of these facial landmarks, and further used to refine the range of permitted orientations of the user device; as if an increase in tension is determined, a smaller range of movement will be permitted to reduce further tension on the user's neck.

In some examples, determining the range of permitted orientations comprises: determining a datum position of the user's head relative to the user device (e.g., calibrating the user's head position and proximity to the user device); and determining, relative to the datum, a range of permitted movement around or along at least one degree of movement of the user's head. In some examples, the at least one degree of movement of the user's head is one or more of: anterior, posterior, ventral, dorsal, right, left, vertical, horizontal, or an anteroposterior axis of the head or a translational movement in one or more of the previous axes.

In a second approach, there is provided a non-transitory computer-readable medium, having instructions recorded thereon which, when executed, cause processing circuitry to carry out a method. The method comprising determining, using control circuitry a current orientation of each of a user's head and a user device; determining an environmental parameter relating to the user's environment; determining a range of permitted orientations of the user's head based on the environmental parameter and the current orientations of the user's head and the user device; determining, using control circuitry, whether the orientation of the user's head is outside of the range of permitted orientations; and in response to determining that the orientation of the user's head is outside of a range of permitted orientations, causing, using control circuitry, a change in a mode of display of the user device.

In a third approach, there is provided a device comprising control circuitry, transceiver circuitry and a display device, configured to: determine, using the control circuitry a current orientation of each of a user's head and a user device; determine an environmental parameter relating to the user's environment; determine a range of permitted orientations of the user's head based on the environmental parameter and the current orientations of the user's head and the user device; determine, using the control circuitry, whether the orientation of the user's head is outside of the range of permitted orientations; and in response to determining that the orientation of the user's head is outside of a range of permitted orientations, cause, using control circuitry, a change in a mode of display of the user device.

In another approach, there is provided a system, the system comprising means for determining, using control circuitry a current orientation of each of a user's head and a user device; means for determining an environmental parameter relating to the user's environment; means for determining a range of permitted orientations of the user's head based on the environmental parameter and the current orientations of the user's head and the user device; means for determining whether the orientation of the user's head is outside of the range of permitted orientations; and in response to determining that the orientation of the user's head is outside of a range of permitted orientations, means for causing a change in a mode of display of the user device.

In another approach, there is provided a method, the method comprising: determining a current gaze point of at least one user's eye and a field of view of the user; determining an environmental parameter relating to the user's environment; determining a range of permitted gaze points of the user's gaze point based on the environmental parameter and the current gaze point of the user's eye and the field of view; determining whether the gaze point of the user's eye is outside of the range of permitted gaze points; and in response to determining that the gaze point of the user's eye is outside of a range of permitted gaze points, causing a change in a mode of display of the user device.

BRIEF DESCRIPTION OF THE DRAWINGS

The above and other objects and advantages of the disclosure will be apparent upon consideration of the following detailed description, taken in conjunction with the accompanying drawings, in which:

FIG. 1 illustrates the effect of headtilt angle and the feels like weight of the head, in accordance with some examples of the disclosure;

FIG. 2 illustrates a visual effect applied to the display of a user device, in accordance with some examples of the disclosure;

DETAILED DESCRIPTION

Figure 3:
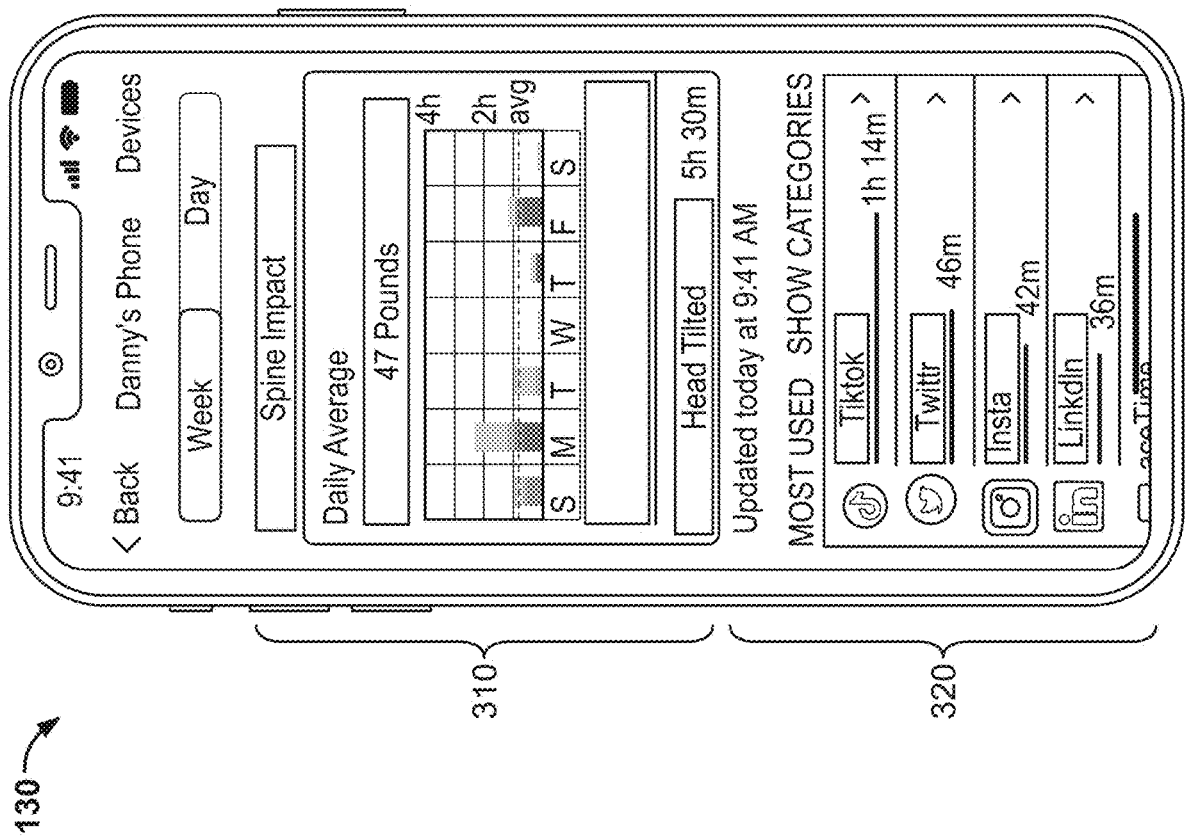
FIG. 3 shows an example data display on a user device, in accordance with some examples of the disclosure.

The predominant use of smartphones and tablets primarily revolves around media consumption, with the most frequently employed applications falling within the categories of social media, gaming, and messaging. To illustrate, Tik-Tok registered over 672 million downloads, Instagram exceeded 548 million downloads, and Facebook garnered more than 449 million downloads worldwide in 2022. Consequently, it is a reasonable deduction that approximately 90% of users' time spent on mobile devices is allocated to engaging with social media, gaming, and entertainment applications. It is worth noting that endeavors to quantify neck movement have been undertaken through the utilization of wearable neck devices. Nevertheless, there exists a palpable demand for an improved solution that obviates the necessity for an additional device to ascertain neck tilt angles.

Furthermore, social media platforms frequently face allegations of contributing to both mental and physical health issues due to the pervasive addiction among consumers. As smart devices have only been in widespread use for slightly over a decade, the manifestation of severe physical health issues resulting from their usage may not yet be fully discernible, but they are anticipated to become increasingly evident in the future.

FIG. 1 illustrates the effect of headtilt angle and the feels like weight of the head, in accordance with some examples of the disclosure. While carpal tunnel syndrome (CTS) is a well-recognized and widely discussed condition, the prevalence of neck pain remains comparatively less acknowledged. This discrepancy in awareness can be attributed to the relatively recent emergence of mobile devices and social media applications, which have not been in existence for as long as the traditional mouse and personal computer platform, where CTS-related issues have received more attention.

As briefly described above, and as FIG. 1 illustrates, the common manner in which individuals utilize their mobile phones, such as user device 130, involves holding the device in a lower position and extending the neck forward to view the screen. It is noteworthy that the degree of neck tilt correlates directly with the resultant pressure exerted on the cervical spine. Specifically, at a 15-degree angle, the pressure on the cervical spine amounts to 27 pounds, escalating to 49 pounds at a 45-degree angle, and peaking at 60 pounds when the tilt angle reaches 60 degrees, as shown in FIG. 1. Prolonged exposure to such spinal pressure, particularly for a duration of 4 hours per day, can significantly contribute to physical harm.

It is pertinent to acknowledge that the incidence of neck pain tends to rise with advancing age. Beyond musculoskeletal discomfort, an inclined head posture can engender a spectrum of other health issues. Seated in a slouched position, individuals may experience limitations in lung expansion, thereby impairing lung capacity. Reduced oxygen intake necessitates the heart to intensify its efforts in pumping blood enriched with oxygen throughout the body.

Extended and prolonged usage of mobile devices in a static posture can give rise to tension in the neck muscles, leading to a reduction in blood flow. This diminished circulation, in turn, results in a lower delivery of oxygen, the accumulation of lactic acid, and the build-up of potentially harmful metabolites. Presently, various applications exist for monitoring vital physiological signals such as heart rate, blood pressure, and oxygen saturation levels from facial video data. In this context, we propose the utilization of a deep learning model to detect alterations in neck muscle tension, leveraging facial and neck area video inputs as well as data acquired from wearables such as smartwatches and finger rings (e.g., Oura).

The present disclosure involves the development of a novel architecture that combines image feature extraction with a temporal attention-based encoder to predict levels of neck muscle tension using facial and neck videos as inputs. The initial step involves the alignment and cropping of facial and neck videos based on facial landmarks. Subsequently, each frame within these videos undergoes processing through a pre-trained image feature extraction model, such as Resnet, which includes trainable layers to allow for fine-tuning based on collected data. The resulting features extracted from the sequence of images are then fed into a temporal attention-based encoder. An additional Multi-Layer Perceptron (MLP) head is incorporated to predict the muscle tension output based on the selected classification token. To facilitate the training of this model, a substantial dataset, comprising corresponding facial and neck videos recorded via mobile phone front cameras, alongside neck muscle tension measurements gathered through electromyography (EMG) sensors is used. Post-training, the proposed deep learning model will possess the capability to estimate neck muscle tension levels from input facial and neck videos to output a screen as shown in FIG. 2.

Once suboptimal posture is detected, the device engages a posture correction algorithm. This algorithm computes the necessary adjustments required for the mobile device screen's pitch and yaw angles to encourage a more ergonomically sound posture. The mobile device screen is then dynamically angled or tilted based on the computed corrections. For instance, if the user's head tilt is beyond a predefined threshold, the device may tilt the screen upward (pitch adjustment) to motivate the user to raise their head. Similarly, if neck muscle tension suggests discomfort, a yaw adjustment may be applied to change the screen's viewing angle.

FIG. 2 illustrates a visual effect applied to the display of a user device, in accordance with some examples of the disclosure.

As the screen adjusts, the user receives visual feedback in real-time, signaling the need for improved posture. This feedback can manifest as a gradual screen tilt, a noticeable change in screen orientation, or even a subtle vibration or directional haptic feedback. If the user fails to adjust their posture in response to the dynamic screen modifications, the device can employ more assertive measures. For instance, it might temporarily pause video playback, halt scrolling in social media apps, or display prominent visual cues to prompt immediate posture correction.

Throughout this process, the device continues to collect data on the user's posture and their response to the dynamic screen adjustments. This data feeds into ongoing machine learning models, refining the system's ability to make accurate posture assessments and provide effective feedback. By employing this method, the mobile device actively contributes to promoting healthier posture habits among users. It combines real-time posture assessment, dynamic screen adjustments, and user feedback to create a proactive and interactive posture correction experience, ultimately supporting the user's well-being and physical health.

FIG. 3 shows an example data display on a user device, in accordance with some examples of the disclosure. In some examples, the operating system or an application of the device 130 assumes the responsibility of quantifying the cumulative instances of head tilt and assessing its potential implications on spinal health. In this way, an application of the device would have access to, and awareness of, application usage and access to sensor data (e.g., IMU, cameras, face recognition technology, and the like). Towards the conclusion of each day, the system initiates a visual alert mechanism directed at the user 100, shown in region 310 of device 130. This alert is additionally accessible through the Health Settings interface, as illustrated in FIG. 3.

In some examples, the device's operating system uses an Application Programming Interface (API), affording individual applications the capability to compute and retain comprehensive time series data pertaining to head tilt occurrences while their respective apps are in use.

Figure 4:
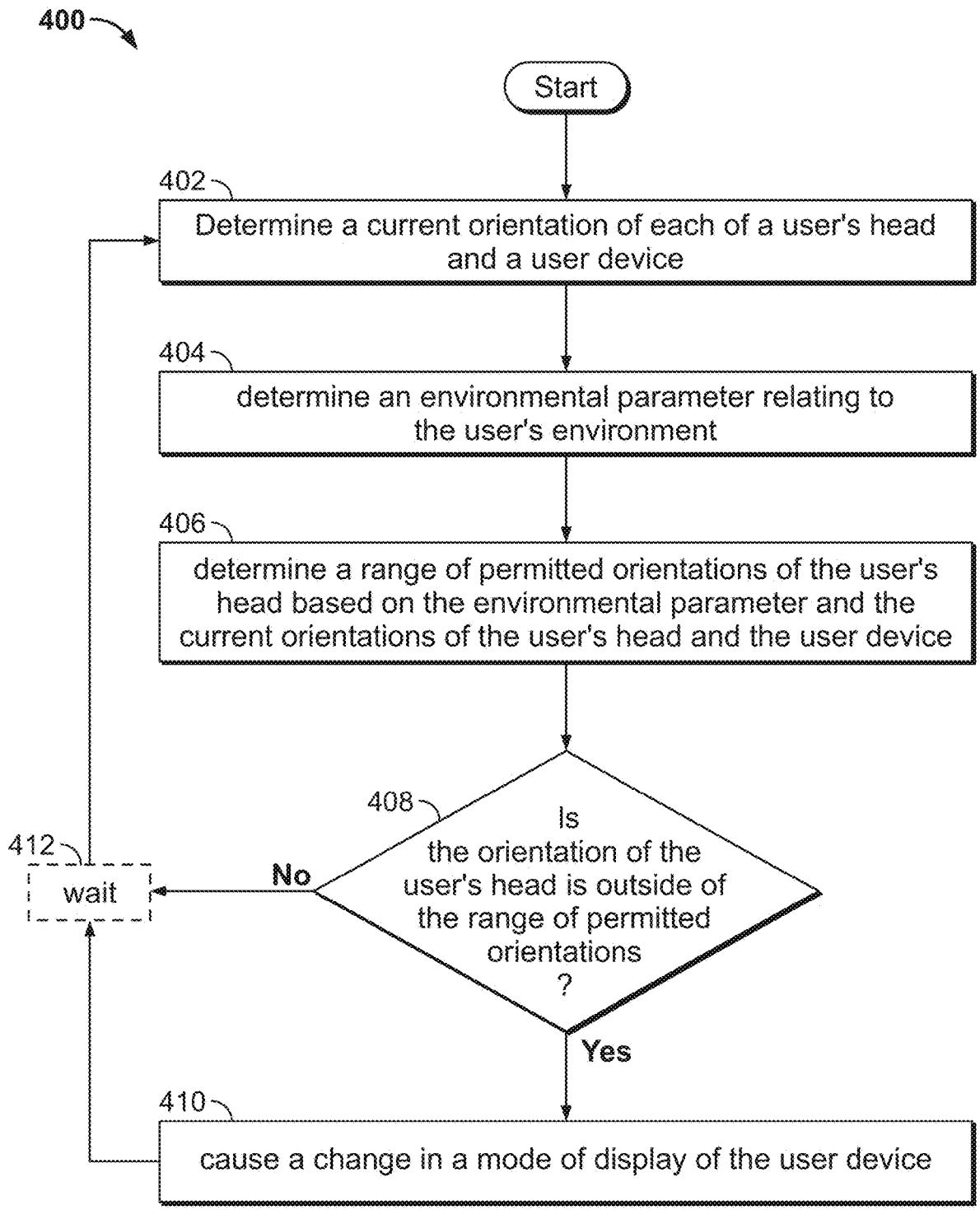
FIG. 4 is an illustrative flowchart of a process, in accordance with some examples of the disclosure.

FIG. 4 is an illustrative flowchart of a process, in accordance with some examples of the disclosure. It should be noted that process 400 or any step thereof could be performed on, or provided by, any of the devices shown in FIGS. 6-8. In addition, one or more steps of process 400 may be incorporated into or combined with one or more steps of any other process or examples described herein (e.g., process 500 (FIG. 5)).

Process 400 begins at step 402. At step 402, process 400 determines a current orientation of each of a user's head and a user device. In some examples, the current orientation of each of a user's head and a user device is determined by a proximity sensor or camera inferring the distance to the user based on facial landmarks and knowledge of the camera properties (e.g., focal length, zoom setting, and the like). For example, it is common place for modern smart phones to have a facial recognition technology to unlock the device. During unlock, a calibration phase can take place. For example, the system can calculate the vertical distance between the head and the shoulders, establishing a foundational metric herein referred to as "HeadSize" in centimeters, which represents the dimensions of the user's head. It should be noted that data generated during this calibration step can be encrypted and stored within a user profile within the operating system or application. This approach eliminates the need for repeated calibration as individuals generally maintain a consistent head size post-childhood, notwithstanding minor variations due to factors such as weight gain.

Subsequently, the proximity sensor or a camera is employed to obtain an initial reading during the calibration process, denoted as "$Prox_{initial}$" in centimeters, signifying the distance between the device screen and the user's face. Periodic readings from the proximity sensor are recorded as "$Proxy_N$." The system then computes the head tilt angle as "90-$T_N$," with "$T_N$" being defined as follows:

For example, taking some data about the user's proximity to the device and their head size during a calibration step, enables the use of trigonometry to determine the user's head tilt angle, $T_N$, as the arccosine of the proximity of the user, $Proxy_N$, over the users head size, HeadSize:

$$T_N = \text{Cosine}^{-1}\left(\frac{Prox_N}{HeadSize}\right)$$

In some examples, enhanced accuracy can be achieved by combining the proximity sensor with an ambient light sensor.

At step 404, process 400 determines an environmental parameter relating to the user's environment. Environmental parameters or contextual factors relating to the user's environment, such as whether the user is standing, sitting, lying down or in a vehicle, alter the effective force the neck feels; as illustrated in FIG. 1, so factoring this information into the present methods allows for a more granular approach that previously possible.

In some examples, the system incorporates the capability to integrate data from adjacent cameras, such as those within a connected home environment, for instance, a camera embedded in a connected TV. These cameras can identify the presence of a couch or chair providing support to the user's neck muscles, in addition to a pose of the user. This additional contextual information is factored into the calculations, enabling the system to readjust and reduce the spinal load imposed on the user.

At step 406, process 400 determines a range of permitted orientations of the user's head based on the environmental parameter and the current orientations of the user's head and the user device. Permitted ranges for a user's neck posture in the context of using a mobile device would ideally align with ergonomic guidelines to ensure comfort, reduce strain, and minimize the risk of musculoskeletal issues.

Here are some example permitted ranges for a user's neck posture when using a mobile device:

Neutral Head Position: The neutral head position is the most relaxed and natural posture for the neck. In this position, the head is aligned with the spine, and the gaze is directed straight ahead. This posture minimizes strain on the neck muscles and is the ideal starting point.

Head Tilt Angle: The head tilt angle, when looking at the mobile device screen, should ideally be within 0 to 30 degrees from the neutral head position. Tilting the head excessively forward or backward can strain the neck.

Horizontal Alignment: The mobile device screen should be at eye level or slightly below eye level when the user's head is in a neutral position. This alignment encourages a straight gaze and reduces the need for excessive neck bending.

Vertical Alignment: The mobile device screen should be positioned in a way that allows the user to maintain a relaxed, upright neck posture. In this way user 100 is encouraged to avoid screens that are too low or too high, as these positions can strain the neck.

Rotation: The user's neck should remain comfortably aligned with the spine, without excessive rotation to one side or the other. Keeping the neck in a neutral position reduces the risk of muscle tension and discomfort.

It is worth noting that the permitted ranges may vary depending on the specific activities being performed on the mobile device. For tasks that require more focused attention, such as reading or typing, users may benefit from a slightly different posture compared to activities like watching videos. Ultimately, the goal is to promote comfort and minimize strain. User 100 is encouraged to adjust their device and posture to align with these general guidelines, while also listening to their own bodies and making further adjustments as needed to maintain a healthy and pain-free neck posture.

At step 408, it is determined whether the orientation of the user's head is outside of the range of permitted orientations. If the answer to step 408 is yes, process 400 continues on to step 410. If the answer to step 408 is no, process 400 continues on to step 412. In some examples, the oscillatory fluctuations in the head's tilt angle, as delineated through the previously discussed methodologies, can be detected. Subsequently, an ancillary weight strain associated with movement-induced head oscillations can be deduced and factored into the overall calculation.

At step 410, process 400 causes a change in a mode of display of the user device 130. For example, the device my alter the pitch, yaw, or angle of the display of the user device 130 as shown in FIG. 2. In some examples, the user is notified of the change in mode of display by way of visual or haptic warnings. In this way, it is made clear to the user what they need to do to remediate the change in mode. In some examples, the cues used for head tilt warning are distinct from those already used on a user device, for messages and the like. In addition, in some examples, the device explicitly informs the user that the reason they are receiving warnings is because of their head tilt posture.

In some examples, when a user fails to rectify their head tilt posture following the issuance of visual and/or haptic warnings, video playback or game execution may be temporarily paused, or the functionality of social media applications may be temporarily suspended, including the disabling of scrolling features. These actions persist until the system detects a corrective head tilt posture. As an alternative or in addition to halting content or applications, other measures, such as reducing the intensity or complexity of game content, can be implemented to encourage improved posture.

In some examples, the device may adjust the presentation of content by proportionally dimming the brightness as the user's head tilt angle relative to the screen decreases. This subtle visual adjustment serves as a gentle nudge to encourage the user to straighten their head posture. Additionally, in an alternative scenario where a user is utilizing smart glasses or virtual reality (VR) device equipped with embedded Inertial Measurement Unit (IMU) sensors, the device can easily calculate the head tilt angle. Consequently, the system can issue audio, visual, or haptic posture change warnings while the user is engaged with their smart glasses or VR device on said glasses or device, or indeed on their primary smart phone or other device; utilizing the aforementioned methodologies.

Overall, change in a mode of the display, including disabling the display (and in some examples maintain audio) in response to poor neck posture is a proactive approach to promoting user health and well-being. It not only mitigates immediate discomfort but also cultivates better posture habits, ultimately contributing to better musculoskeletal health and reducing the risk of long-term posture-related issues.

At step 412, an optional wait period is initiated for a configurable time period. After the wait period has expired process 400 reverts back to step 402. If the waiting period isn't initiated, process 400 may revert to step 402 immediately. In this way, process 400 repeats. In some examples, step 412 is an optional confirmation window, in this way it can be confirmed that the threshold is crossed and remains crossed for a configurable period of time.

Figure 5:
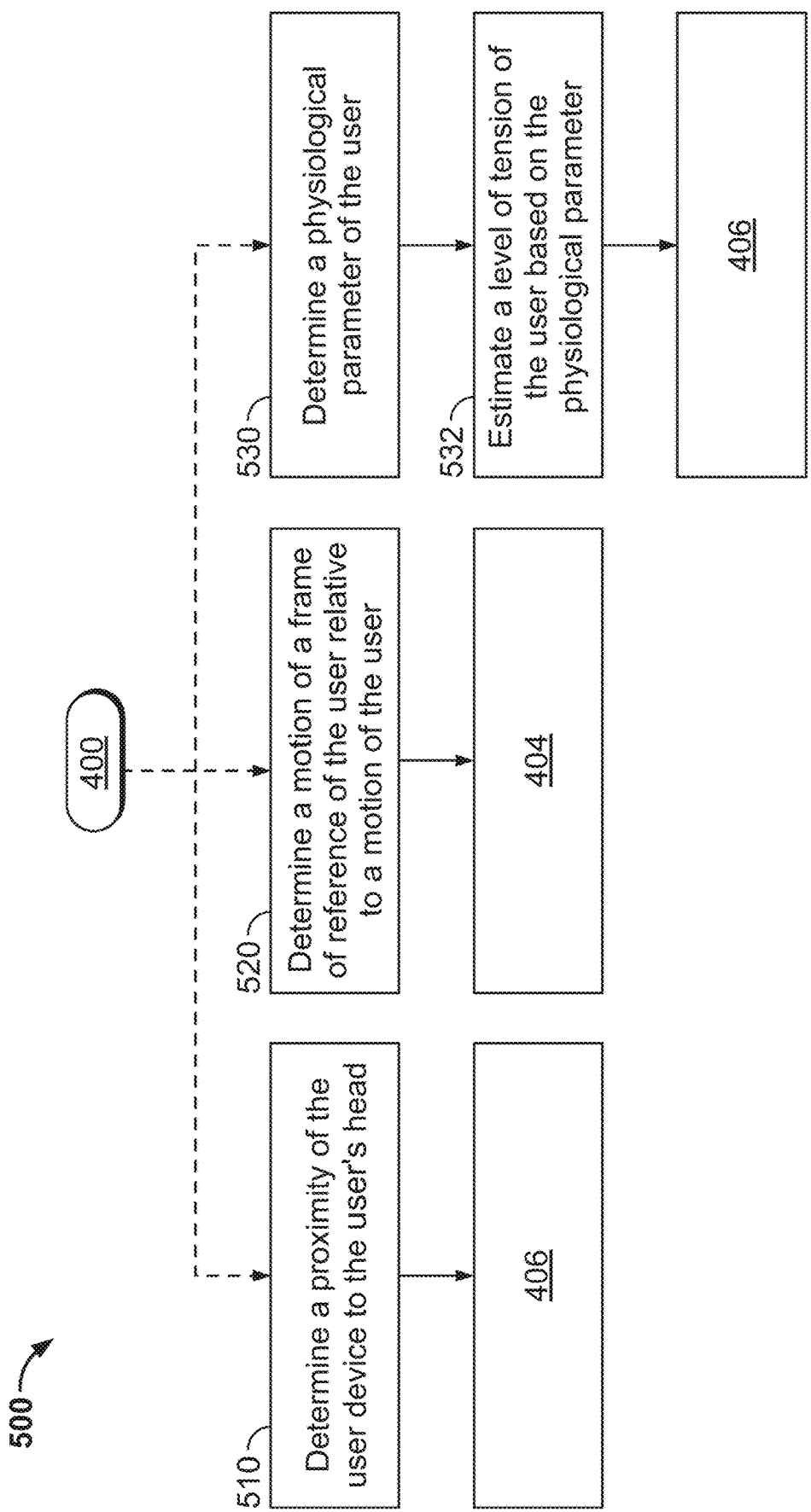
FIG. 5 is an illustrative flowchart of a process, in accordance with some examples of the disclosure.

FIG. 5 is an illustrative flowchart of a process, in accordance with some examples of the disclosure. It should be noted that process 500 or any step thereof could be performed on, or provided by, any of the devices shown in FIGS. 6-8. In addition, one or more steps of process 500 may be incorporated into or combined with one or more steps of any other process or examples described herein (e.g., process 400 (FIG. 4)).

At step 510, process 500 describes determining a proximity of the user device to the user's head. After step 510, process 500 continues on to step 406 of process 400 such that the determining the range of permitted orientations is further based on the proximity of the user device to the user's head.

The proximity of the user's device to their head can significantly impact their neck posture and overall comfort while using the device. For example, the closer the device is to the user's head, the more likely it is that the user will adopt a posture that involves bending their neck forward or looking down. This can lead to increased neck strain, as the neck muscles have to work harder to support the head in this position. In another example, proximity to the head can influence the angle at which the user tilts their head. If the device is very close, the user may tilt their head at a steeper angle to view the screen, increasing the strain on the neck. Furthermore, when the device is very close to the user's head, it can also lead to eye strain, as the eyes have to work harder to focus on a nearby screen for extended periods. This can cause discomfort and fatigue.

Users tend to adapt their posture based on the device's proximity. If the device is held close, they may slouch or hunch their shoulders to get a better view. Conversely, if the device is farther away, they may sit or stand with better posture.

At step 520, process 500 describes determining a motion of a frame of reference of the user relative to a motion of the user. After step 520, process 500 continues on to step 404 of process 400 such that determining the environmental parameter relating to the user's environment is further based on the motion of a frame of reference of the user relative to a motion of the user.

At step 530, process 500 describes determining a physiological parameter of the user. At step 532, process 500 describes estimating a level of tension of the user based on the physiological parameter. In some examples, process 500 also comprises determining a change in a position of a facial landmark of the user. After step 532, process 500 continues on to step 406 of process 400 such that the determining the range of permitted orientations is further based on the estimated level of tension.

Utilizing physiological parameters to determine fatigue in the neck while using a mobile device involves monitoring various bodily indicators that can indirectly reflect the user's neck fatigue. For example, electromyography (EMG) sensors can directly measure muscle activity. Increased muscle tension and prolonged muscle activation in the neck muscles can indicate fatigue. When the system detects elevated EMG signals from the neck muscles over a certain threshold, it may infer that neck fatigue is likely.

Moreover, monitoring blood oxygen saturation levels (SpO2) can provide insights into overall circulatory health. Neck fatigue can potentially reduce blood flow to the muscles, affecting oxygen delivery. A consistent decrease in SpO2 levels while using a mobile device may suggest neck muscle fatigue. In addition, heart rate variability, HRV, which measures the variation in time between consecutive heartbeats, can reflect the autonomic nervous system's balance. High stress levels can lead to increased sympathetic nervous system activity. A sustained increase in HRV patterns indicative of stress may suggest neck fatigue.

Furthermore, Lactic acid is a metabolic byproduct produced during intense muscle activity when oxygen supply is insufficient. Elevated lactic acid levels in the bloodstream can signal muscle fatigue. Continuous monitoring of lactic acid levels in combination with neck muscle activity data can provide insights into neck fatigue. In addition, changes in skin conductance can indicate stress levels. Increased stress due to neck fatigue can lead to alterations in skin conductance. Integrating this data with other physiological parameters can help assess neck fatigue.

Figure 6:
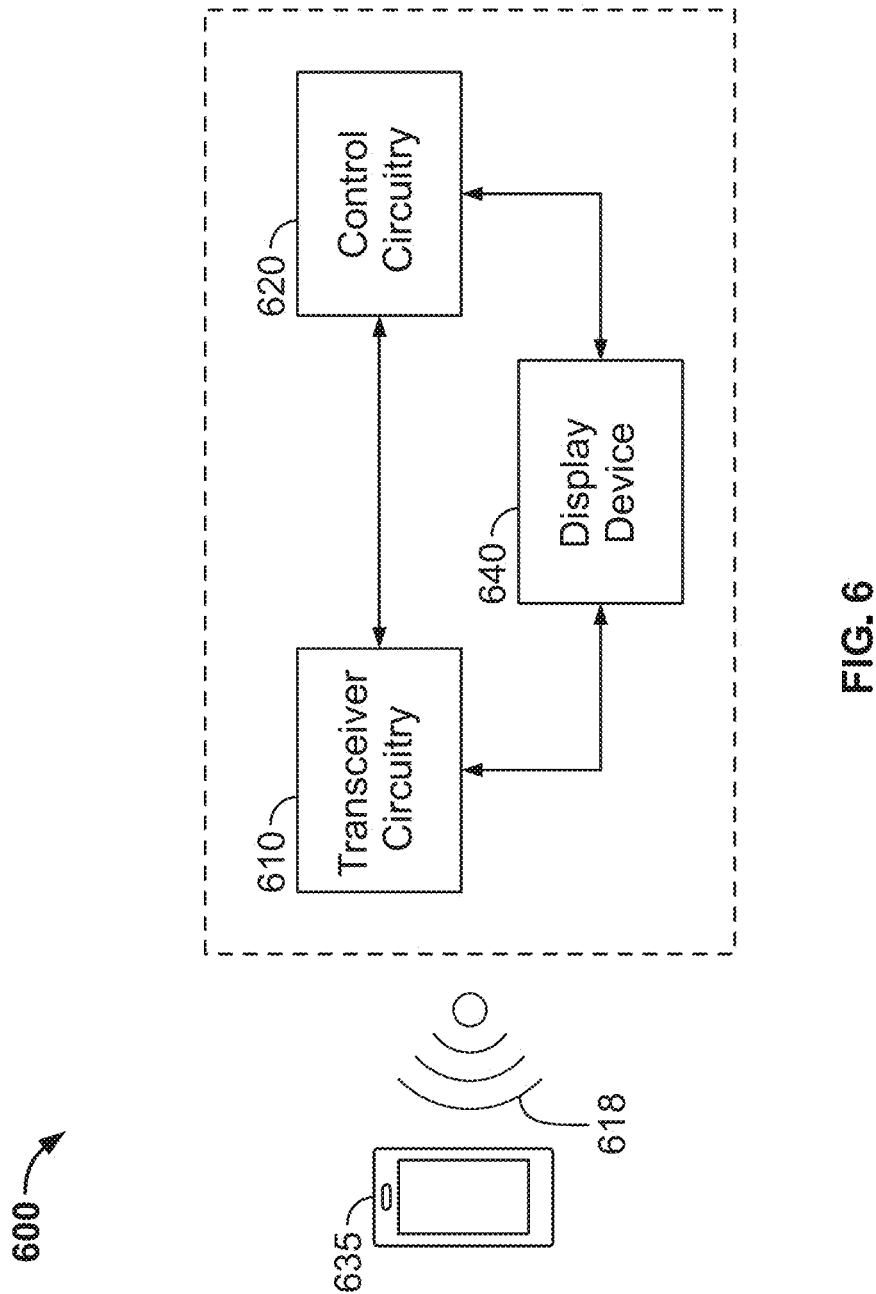
FIG. 6 illustrates an exemplary media transmission device, in accordance with some examples of the disclosure.

FIG. 6 illustrates an exemplary media device 600, in accordance with some examples of the disclosure. The media device 600 comprises transceiver circuitry 610, control circuitry 620, and a display device 640. In some examples, the media device 600 is a user device. The control circuitry 620 is configured to determine a current orientation of each of a user's head and the user device; determine an environmental parameter relating to the user's environment; determine a range of permitted orientations of the user's head based on the environmental parameter and the current orientations of the user's head and the user device; determine whether the orientation of the user's head is outside of the range of permitted orientations; and in response to determining that the orientation of the user's head is outside of a range of permitted orientations, cause a change in a mode of display of the display device 640.

The media device may communicate with an additional user device 635, such as a car vehicle system, personal computer, physiological sensor, smartphone, or other smart devices. In some examples, the transceiver circuitry communicates with the additional user device 635 via communication link 618. For example, the transceiver circuitry 610 of device 600 is configured to enable a continuation of a level of user interaction by handing off the current user interaction to the additional user device 635.

The communication link 618 between the transceiver circuitry 610 and the second user device 635 may comprise a physical connection, facilitated by an input port such as a 3.5 mm jack, RCA jack, USB port, ethernet port, or any other suitable connection for communicating over a wired connection or may comprise a wireless connection via BLUETOOTH, Wi-Fi, WiMAX, Zigbee, GSM, UTMS, CDMA, TDMA, 3G, 4G, 4G LTE, 5G or other wireless transmissions as described by the relevant 802.11 wireless communication protocols.

In some examples, the second user device 635 may receive a physiological parameter of the user and then transmit the physiological parameter to the device 600. In some examples, after receiving a physiological parameter of the user, the device 130 estimates a level of tension of the user based on the physiological parameter and determining the range of permitted orientations is further based on the estimated level of tension. However, these examples are considered to be non-limiting and other combinations of the features herein being spread over two or more devices are considered within the scope of this disclosure. For example, each of the transceiver circuitry, the display device, and the control circuitry may be separate internet of things (IoT) devices that each carry out a portion of the methods herein. Collectively, these devices may be referred to as a system.

The media device 600 and/or user device 635 may collectively be a vehicle system, or virtual reality headset. In such an example, an eye contact detection component, which may be a part of control circuitry 620, may be used to identify the gaze point of a user, in order to determine whether or not a user is focusing on a particular portion of an environment and/or determine a line of sight or field of view a user and/or avatar. For example, the location upon which a user's eyes are focused may determine whether or not the system causes a change in a mode of display of the display device.

Figure 7:
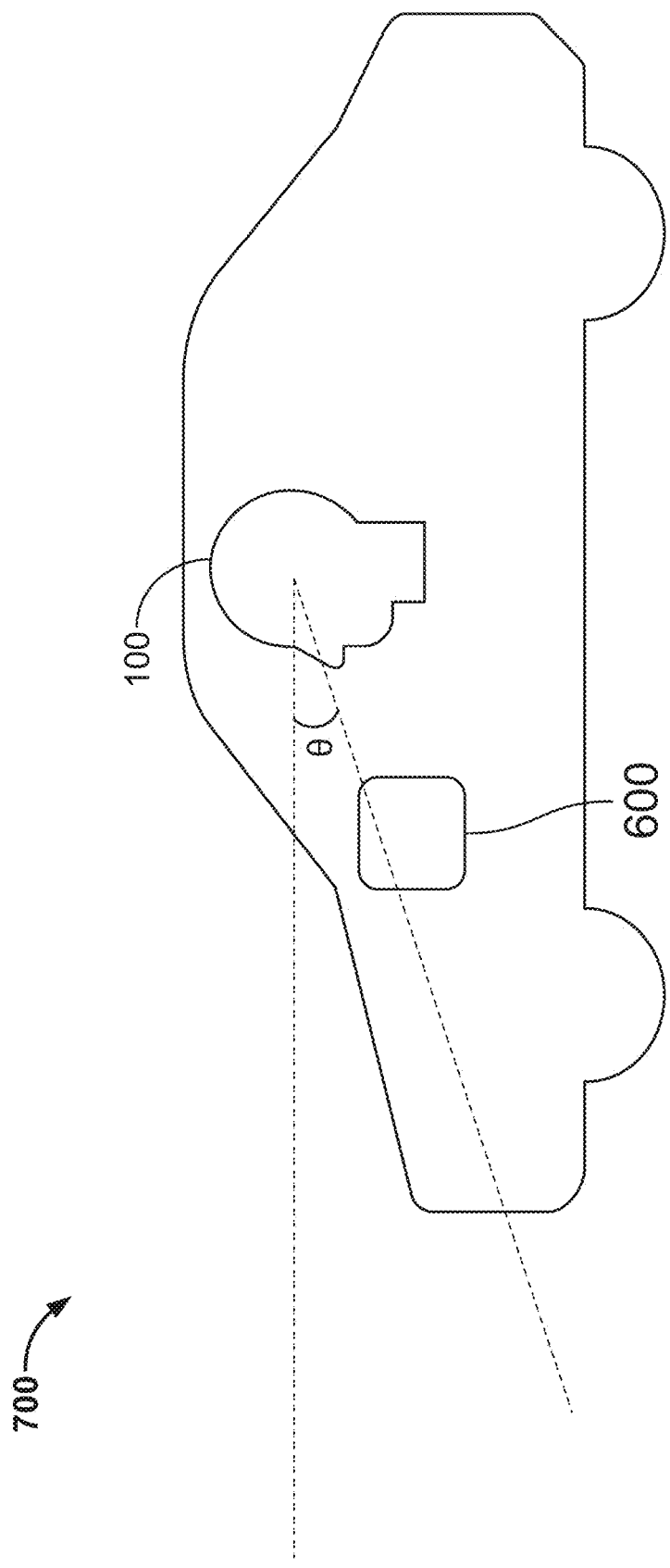
FIG. 7 is a pictoral representation of a user in a vehicle, in accordance with some examples of the disclosure.

FIG. 7 is a pictoral representation of a user in a vehicle, in accordance with some examples of the disclosure. While the user 100 is operating the vehicle 700, they may be distracting by the user device 600. In some examples, where the user device is a vehicle system, instead of an orientation of the user's head being determined, it is the user's gaze point that is determined. In such an example the method carried out by the vehicle comprises: determining a current gaze point of at least one user's eye and a field of view of the user; determining an environmental parameter relating to the user's environment; determining a range of permitted gaze points of the user's gaze point based on the environmental parameter and the current gaze point of the user's eye and the field of view; determining whether the gaze point of the user's eye is outside of the range of permitted gaze points; and in response to determining that the gaze point of the user's eye is outside of a range of permitted gaze points, causing a change in a mode of display of the user device.

In some examples, akin issues related to head tilt angles and postures can be identified through in-cabin monitoring cameras within vehicles, particularly during extended journeys or instances when the driver's attention is directed toward the dashboard or infotainment screen. When persistent forward head posture is detected over prolonged periods, the system responds by implementing haptic feedback on the steering wheel, simultaneously delivering visual cues on the windshield, or issuing auditory warnings to the driver as a precautionary measure.

In some examples, refinements to the weight of strain formula are introduced to account for localized accelerations and supplementary momentum effects that arise from head tilting while situated within a moving vehicle. To illustrate, the device under interaction may employ its Inertial Measurement Unit (IMU) to assess local accelerations within the reference frame of the user's spine. This assessment facilitates the calculation of additional applied strain exerted on the spine, attributed to the oscillatory motion of the head induced by the vehicular movements.

Figure 8:
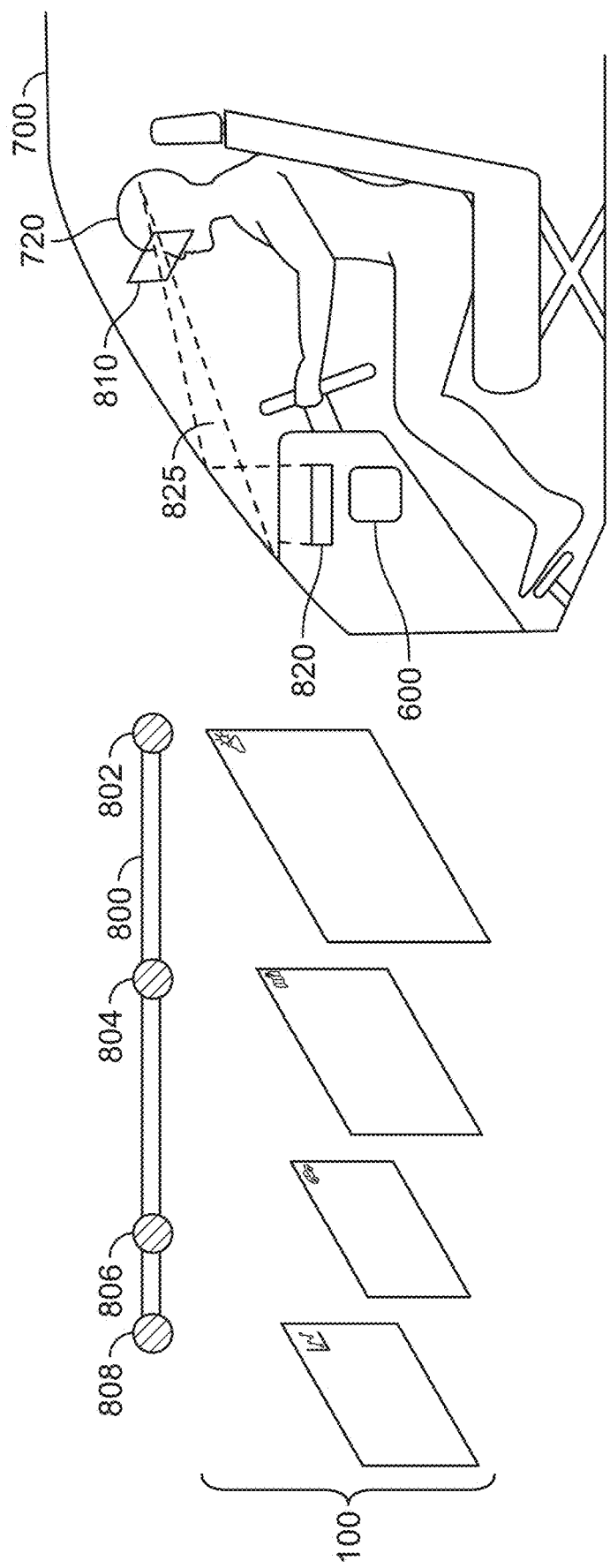
FIG. 8 is a pictoral representation of a user in a vehicle and a heads-up display, in accordance with some examples of the disclosure.

FIG. 8 is a pictoral representation of a user in a vehicle and a heads-up display, in accordance with some examples of the disclosure. Illustrated is a representative scroll bar 800, a plurality of graphical elements 100, and a vehicle 700. Shown inside the vehicle is a user 720, operating the vehicle 700, a view box 810 of the user, a head-up display device 820, and a lightbox 825 of the head-up display device 820. It should be noted that the view box 810 and the lightbox 825 are intended to represent the user's field of view and the path of light leaving the head-up display, respectively. The image of the plurality of graphical elements 100 is substantially transparent in the windscreen head-up display of vehicle 700.

The vehicle 700 includes a steering wheel and a central column, wherein the user device 130 may be disposed. The vehicle may comprise an information system for the vehicle, which may operate in addition to, or in lieu of, other instruments and control features in the vehicle. The vehicle may also comprise a computer for handling informational data, including vehicle data. The computer also includes other necessary electronic components known to those skilled in the art, such as a memory, a hard drive, communication interfaces, a power supply/converter, digital and analog converters, etc. The computer is connected to vehicle systems that provide the vehicle data which corresponds to the operation of the vehicle and associated vehicle systems. Examples of these vehicle systems, include, but are not limited to, an engine controller, a climate control system, an integrated cellular phone system, a sound system (radio), a global positioning system (GPS) receiver, and a video entertainment center (such as a DVD player). Examples of vehicle data provided by the vehicle systems include, but are not limited to, vehicle speed, engine RPM, engine oil pressure, engine coolant temperature, battery voltage, vehicle maintenance reminders, climate control system settings, outside temperature, radio settings, integrated cellular phone settings, compass headings, video images, sound files, digital radio broadcasts, state of charge of both high and low voltage batteries (e.g., 48V hybrid battery, 12V infotainment battery, etc.), and navigational information. All of the former information data, vehicle data, and vehicle systems may have a corresponding graphical element that may be represented on the head-up display, by head-up display device 820.

The informational data handled by the computer can also include external data from a network external to the vehicle. In this case, an external wireless interface would be operatively connected to the computer to communicate with the network for sending and receiving external data. External data may include, but is not limited to, internet web pages, email, and navigational information, handing off to the vehicle system computer by the user device 600.

Figure 9:
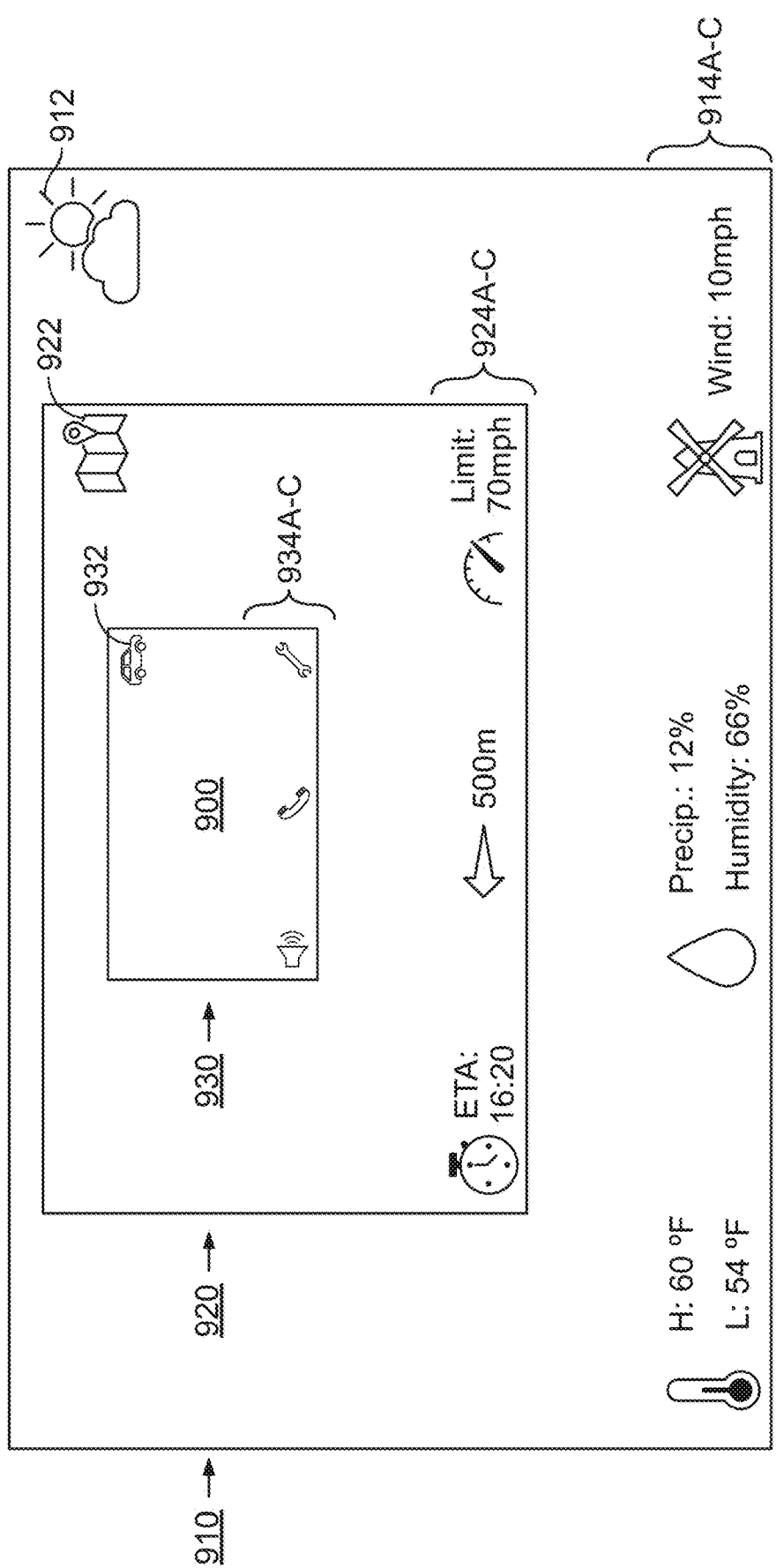
FIG. 9 is a pictoral representation of a heads-up display in a vehicle, in accordance with some examples of the disclosure.

The head-up display device 825 emits light that enters the user's eye by reflecting off the windscreen of the vehicle 700. This gives a holographic image in the windscreen that the user can see. The head-up display device is configured to provide a perceived depth of the plurality of graphical elements 100 from the user's 720 perspective. FIG. 9 illustrates exemplary planes of a head-up display that a user 720 might possibly observe in the vehicle 700. Each of the planes 910-930 comprise a plurality of information data.

Figure 10:
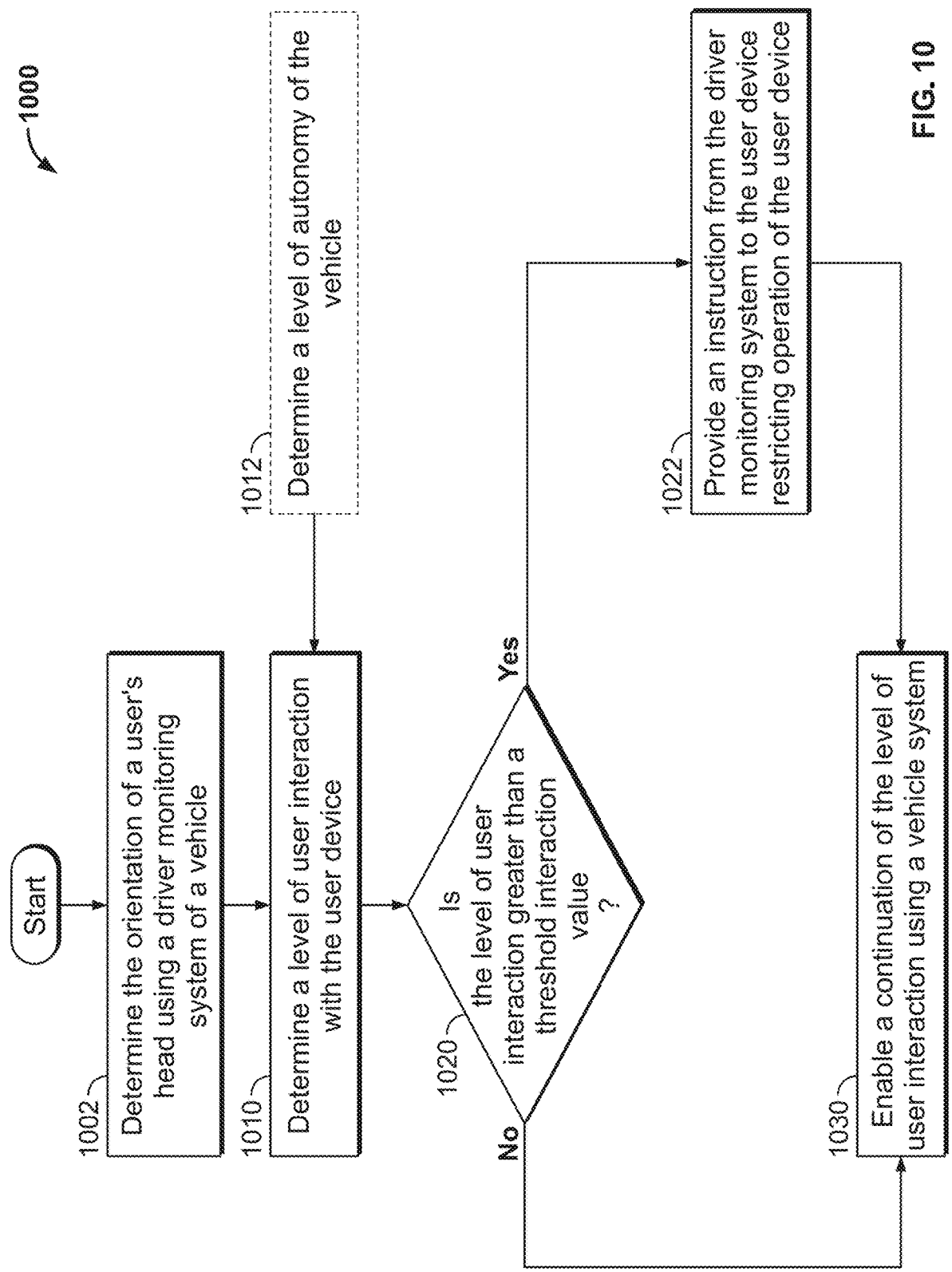
FIG. 10 is an illustrative flowchart of a process, in accordance with some examples of the disclosure.

For example, plane 910 is a weather plane, as indicated by weather icon 912. The weather plane 910 contains a plurality of displayable data 914A-C comprising, for example, windscreen, precipitation, and temperature data. The second plane 920 is a navigation plane, as indicated by the navigation icon 922. The navigation plane 920 contains a plurality of displayable data 924A-C comprises, for example, speed limit information, navigation instructions, and the estimated time of arrival. The third plane 930 is a vehicle information plane, as indicated by vehicle information icon 132. The vehicle information plane 930 contains a plurality of displayable data 934A-C comprising, for example, a settings submenu, a communication submenu, and volume control. Accordingly, user 710 can quickly see at a glance a plurality of information relating to many vehicle systems. In some examples, the displayable data is only present on the foremost plane, and only the icons are displayable from the other planes, to prevent a cluttered head-up display and detracted from the user's action, for example driving. In some examples, the information displayed on the heads-up display is that handed off from user device FIG. 10 is an illustrative flowchart of a process, in accordance with some examples of the disclosure. It should be noted that process 1000 or any step thereof could be performed on, or provided by, any of the devices shown in FIGS. 6-8. In addition, one or more steps of process 1000 may be incorporated into or combined with one or more steps of any other process or examples described herein. Process 1000 starts at step 1002.

At step 1002, process 1000 determines the orientation of a user's head using a driver monitoring system of a vehicle via, for example, an in cabin camera system. At step 1010, process 1000 determines a level of user interaction with the user device. Optionally, at step 1012, process 1000 determines a level of autonomy of the vehicle, and in some examples, the interaction value is based on the level of autonomy.

At step 1020, process 1000 determines if the level of user interaction greater than a threshold interaction value. If the answer to step 1020 is yes, process 1000 continues on to step 1022. If the answer to step 1020 is no, process 1000 continues on to step 1030. At step 1022, process 1000 provides an instruction from the driver monitoring system to the user device restricting operation of the user device via, for example, a Bluetooth, NFC, Wi-Fi, or other wireless or wired communication protocol. At step 1030, process 1000 enables a continuation of the level of user interaction using a vehicle system.

Figure 11:
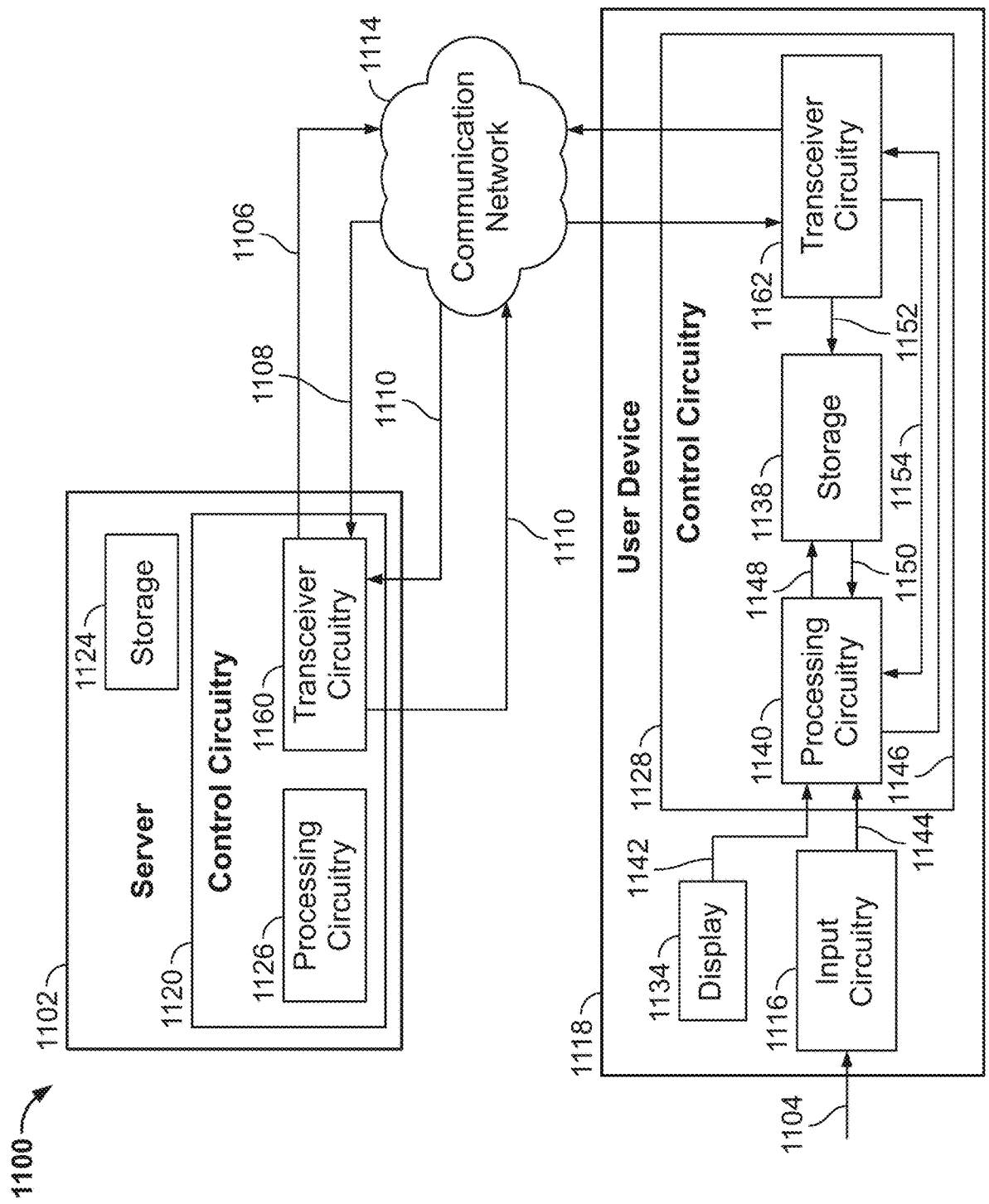
FIG. 11 is a block diagram representing devices, components of each device, and data flow therebetween for a system, in accordance with some examples of the disclosure.

FIG. 11 is a block diagram representing devices, components of each device, and data flow therebetween for a system, in accordance with some examples of the disclosure. System 1100 is shown to include a user device 1118, a server 1102, and a communication network 1114. It is understood that while a single instance of a component may be shown and described relative to FIG. 11, additional instances of the component may be employed. For example, server 1102 may include or may be incorporated in, more than one server. Similarly, communication network 1114 may include or may be incorporated in, more than one communication network. Server 1102 is shown communicatively coupled to user device 1118 through communication network 1114. While not shown in FIG. 11, server 1102 may be directly communicatively coupled to user device 1118, for example, in a system absent or bypassing communication network 1114. User device 1118 may be thought of as the user device 130, 600 or 635. as described above.

Communication network 1114 may comprise one or more network systems, such as, without limitation, an internet, LAN, WIFI, or other network systems suitable for audio processing applications. In some examples, system 1100 excludes server 1102, and functionality that would otherwise be implemented by server 1102 is instead implemented by other components of system 1100, such as one or more components of communication network 1114. In still other examples, server 1102 works in conjunction with one or more components of a communication network 1114 to implement certain functionality described herein in a distributed or cooperative manner. Similarly, in some examples, system 1100 excludes user device 1118, and functionality that would otherwise be implemented by the user device 1118 is instead implemented by other components of system 1100, such as one or more components of communication network 1114 or server 1102 or a combination. In still other examples, the user device 1118 works in conjunction with one or more components of communication network 1114 or server 1102 to implement certain functionality described herein in a distributed or cooperative manner.

The user device 1118 includes control circuitry 1128, display 1134, and input-output circuitry 1116. Control circuitry 1128, in turn, includes transceiver circuitry 1162, storage 1138, and processing circuitry 1140. In some examples, user device 1118 or control circuitry 1128 may be configured as user device 1135 of FIG. 11.

Server 1102 includes control circuitry 1120 and storage 1124. Each of storage 1124 and 1138 may be an electronic storage device. As referred to herein, the phrase "electronic storage device" or "storage device" should be understood to mean any device for storing electronic data, computer software, or firmware, such as random-access memory, read-only memory, hard drives, optical drives, digital video disc (DVD) recorders, compact disc (CD) recorders, BLU-RAY disc (BD) recorders, BLU-RAY 3D disc recorders, digital video recorders (DVRs, sometimes called personal video recorders, or PVRs), solid-state devices, quantum storage devices, gaming consoles, gaming media, or any other suitable fixed or removable storage devices, and/or any combination of the same. Each storage 1124, 1138 may be used to store various types of content, media data, and or other types of data (e.g., they can be used to store media content such as audio, video, and advertisement data). The non-volatile memory may also be used (e.g., to launch a boot-up routine and other instructions). Cloud-based storage may be used to supplement storages 1124, 1138 or instead of storages 1124, 1138. In some examples, the pre-encoded or encoded media content, in accordance with the present disclosure, may be stored on one or more of storages 1124, 1138.

In some examples, control circuitry 1120 and/or 1128 executes instructions for an application stored on the memory (e.g., storage 1124 and/or storage 1138). Specifically, control circuitry 1120 and/or 1128 may be instructed by the application to perform the functions discussed herein. In some implementations, any action performed by control circuitry 1120 and/or 1128 may be based on instructions received from the application. For example, the application may be implemented as software or a set of executable instructions that may be stored on storage 1124 and/or 1138 and executed by control circuitry 1120 and/or 1128. In some examples, the application may be a client/server application where only a client application resides on user device 1118, and a server application resides on server 1102.

The application may be implemented using any suitable architecture. For example, it may be a stand-alone application wholly implemented on user device 1118. In such an approach, instructions for the application are stored locally (e.g., in storage 1138), and data for use by the application is downloaded periodically (e.g., from an out-of-band feed, from an internet resource, or using another suitable approach). Control circuitry 1128 may retrieve instructions for the application from storage 1138 and process the instructions to perform the functionality described herein. Based on the processed instructions, control circuitry 1128 may determine a type of action to perform in response to input received from the input/output path (or input-output circuitry) 1116 or the communication network 1114. For example, in response to a receiving a natural language input on the user device 1118, control circuitry 1128 may perform the steps of processes as described with reference to various examples discussed herein.

In client/server-based examples, control circuitry 1128 may include communication circuitry suitable for communicating with an application server (e.g., server 1102) or other networks or servers. The instructions for carrying out the functionality described herein may be stored on the application server. Communication circuitry may include a cable modem, an Ethernet card, or a wireless modem for communication with other equipment, or any other suitable communication circuitry. Such communication may involve the internet or any other suitable communication networks or paths (e.g., communication network 1114). In another example of a client/server-based application, control circuitry 1128 runs a web browser that interprets web pages provided by a remote server (e.g., server 1102). For example, the remote server may store the instructions for the application in a storage device. The remote server may process the stored instructions using circuitry (e.g., control circuitry 1128) and/or generate displays. User device 1118 may receive the displays generated by the remote server and may display the content of the displays locally via display 1134. This way, the processing of the instructions is performed remotely (e.g., by server 1102) while the resulting displays, such as the display windows described elsewhere herein, are provided locally on the user device 1118. User device 1118 may receive inputs from the user via input circuitry 1116 and transmit those inputs to the remote server for processing and generating the corresponding displays. Alternatively, user device 1118 may receive inputs from the user via input circuitry 1116 and process and display the received inputs locally, by control circuitry 1128 and display 1134, respectively.

It is understood that user device 1118 is not limited to the examples and methods shown and described herein. In non-limiting examples, the user device 1118 may be a digital storage device, a streaming media device, a personal computer (PC), a laptop computer, a tablet computer, a PC media server, a handheld computer, a mobile telephone, a portable gaming machine, a smartphone, a virtual reality headset, an augmented reality headset, a mixed reality headset, or any other device, client equipment, or wireless device, and/or combination of the same capable of carry out the methods herein.

Control circuitry 1120 and/or 1118 may be based on any suitable processing circuitry such as processing circuitry 1126 and/or 1140, respectively. As referred to herein, processing circuitry should be understood to mean circuitry based on one or more microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, or any suitable number of cores). In some examples, processing circuitry may be distributed across multiple separate processors, for example, multiple of the same type of processors (e.g., two Intel Core i9 processors) or multiple different processors (e.g., an Intel Core i7 processor and an Intel Core i9 processor). In some examples, control circuitry 1120 and/or control circuitry 1118 are configured to alleviate neck pain during media consumption or keep a user's gaze away from a user device, such as systems, or parts thereof, that perform various processes described herein.

User device 1118 receives a user input 1104 at input circuitry 1116. For example, user device 1118 may receive a user input like a user swipe, user touch, or input from peripherals such as a keyboard and mouse, gaming controller, or the like. It is understood that user device 1118 is not limited to the examples and methods shown and described herein. In non-limiting examples, the user device 1118 may be a a personal computer (PC), a laptop computer, a tablet computer, a a handheld computer, a mobile telephone, a portable gaming machine, a smartphone, virtual reality headset, mixed reality headset, an augmented reality headset, or any other computing equipment, or wireless device, and/or combination of the same.

User input 1104 may be received from a user selection-capturing interface that is separate from device 1118, such as a remote-control device, trackpad, or any other suitable user movement sensitive or capture devices, or as part of device 1118, such as a touchscreen of display 1134. Transmission of user input 1104 to user device 1118 may be accomplished using a wired connection, such as an audio cable, USB cable, ethernet cable, or the like attached to a corresponding input port at a local device, or may be accomplished using a wireless connection, such as BLUETOOTH, Wi-Fi, WiMAX, ZIGBEE, GSM, UTMS, CDMA, TDMA, 3G, 4G, 4G LTE, 5G, or any other suitable wireless transmission protocol. Input circuitry 1116 may comprise a physical input port such as a 3.5 mm audio jack, RCA audio jack, USB port, ethernet port, or any other suitable connection for receiving audio over a wired connection, or may comprise a wireless receiver configured to receive data via BLUETOOTH, Wi-Fi, WiMAX, ZIGBEE, GSM, UTMS, CDMA, TDMA, 3G, 4G, 4G LTE, 5G, or other wireless transmission protocols.

Processing circuitry 1140 may receive input 1104 from input circuit 1116. Processing circuitry 1140 may convert or translate the received user input 1104 that may be in the form of gestures or movement to digital signals. In some examples, input circuit 1116 performs the translation to digital signals, which are then used in processing. In some examples, processing circuitry 1140 (or processing circuitry 1126, as the case may be) carries out disclosed processes and methods.

The system described above with reference to FIG. 11 has the means to carry out a method, which when executed causes control circuitry to: determine a current orientation of each of a user's head and the user device; determine an environmental parameter relating to the user's environment; determine a range of permitted orientations of the user's head based on the environmental parameter and the current orientations of the user's head and the user device; determine whether the orientation of the user's head is outside of the range of permitted orientations; and in response to determining that the orientation of the user's head is outside of a range of permitted orientations, cause a change in a mode of display of the display device.

The systems and processes discussed above are intended to be illustrative and not limiting. One skilled in the art would appreciate that the actions of the processes discussed herein may be omitted, modified, combined, and/or rearranged, and any additional actions may be performed without departing from the scope of the invention. More generally, the above disclosure is meant to be exemplary and not limiting. Only the claims that follow are meant to set bounds as to what the present disclosure includes. Furthermore, it should be noted that the features and limitations described in any one example may be applied to any other example herein, and flowcharts or examples relating to one example may be combined with any other example appropriately, done in different orders, or done in parallel. In addition, the systems and methods described herein may be performed in real-time. It should also be noted that the systems and/or methods described above may be applied to, or used in accordance with, other systems and/or methods. In this specification, the following terms may be understood given the below explanations:

All of the features disclosed in this specification (including any accompanying claims, abstract, and drawings), and/or all of the steps of any method or process so disclosed, may be combined in any combination, except combinations where at least some of such features and/or steps are mutually exclusive.

Each feature disclosed in this specification (including any accompanying claims, abstract, and drawings), may be replaced by alternative features serving the same, equivalent or similar purpose unless expressly stated otherwise. Thus, unless expressly stated otherwise, each feature disclosed is one example only of a generic series of equivalent or similar features.

The invention is not restricted to the details of any foregoing examples. The invention extends to any novel one, or any novel combination, of the features disclosed in this specification (including any accompanying claims, abstract, and drawings), or to any novel one, or any novel combination, of the steps of any method or process so disclosed. The claims should not be construed to cover merely the foregoing examples, but also any examples which fall within the scope of the claims.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing examples. The invention extends to any novel one, or any novel combination, of the features disclosed in this specification (including any accompanying claims, abstract, and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

What is claimed is:

1. A method comprising:
   determining, using control circuitry, a current orientation of each of a user's head and a user device;
   determining a change in a position of a facial landmark of the user;
   estimating a level of tension of the user based on the change in a position of the facial landmark of the user;
   determining an environmental parameter relating to the user's environment;
   determining a range of permitted orientations of the user's head based on the estimated level of tension, the environmental parameter, and the current orientations of the user's head and the user device;
   determining, using control circuitry, whether the orientation of the user's head is outside of the range of permitted orientations; and
   in response to determining that the orientation of the user's head is outside of the range of permitted orientations, causing, using control circuitry, a change in a mode of display of the user device.

2. The method of claim 1, the method comprising:
   determining a proximity of the user device to the user's head, wherein determining the range of permitted orientations is further based on the proximity of the user device to the user's head.

3. The method of claim 1, wherein determining the environmental parameter relating to the user's environment comprises:
   determining a motion of a frame of reference of the user relative to a motion of the user device.

4. The method of claim 1, the method comprising determining the orientation of a user's head using a monitoring system of a vehicle.

5. The method of claim 4, the method comprising:
   determining a level of user interaction with the user device; and
   receiving, at the user device, an instruction from the monitoring system of the vehicle restricting operation of the user device when the level of user interaction is greater than an interaction value.

6. The method of claim 5, the method further comprising:
   enabling a continuation of the level of user interaction using a vehicle system, while the operation of the user device is restricted.

7. The method of claim 5, the method further comprising:
   determining a level of autonomy of the vehicle, wherein the interaction value is based on the level of autonomy of the vehicle.

8. The method of claim 1, the method comprising:
   determining a physiological parameter of the user; and
   estimating the level of tension of the user based on the physiological parameter.

9. The method of claim 1, wherein determining the range of permitted orientations comprises:
   determining a datum position of the user's head relative to the user device; and
   determining, relative to the datum, a range of permitted movement around or along at least one degree of movement of the user's head.

10. A system comprising control circuitry, the control circuitry configured to:
    determine a current orientation of each of a user's head and a user device;
    determine a change in a position of a facial landmark of the user;
    estimate a level of tension of the user based on the change in a position of the facial landmark of the user;
    determine an environmental parameter relating to the user's environment;
    determine a range of permitted orientations of the user's head based on the estimated level of tension, the environmental parameter, and the current orientations of the user's head and the user device;
    determine, using control circuitry, whether the orientation of the user's head is outside of the range of permitted orientations; and
    in response to determining that the orientation of the user's head is outside of the range of permitted orientations, cause, using control circuitry, a change in a mode of display of the user device.

11. The system of claim 10, the control circuitry configured to:
    determine a proximity of the user device to the user's head, wherein determining the range of permitted orientations is further based on the proximity of the user device to the user's head.

12. The system of claim 10, wherein determining the environmental parameter relating to the user's environment comprises:
    determining a motion of a frame of reference of the user relative to a motion of the user device.

13. The system of claim 10, the control circuitry configured to determine the orientation of a user's head using a monitoring system of a vehicle.

14. The system of claim 13, the control circuitry configured to:
    determine a level of user interaction with the user device; and
    receive, at the user device, an instruction from the monitoring system of the vehicle restricting operation of the user device when the level of user interaction is greater than an interaction value.

15. The system of claim 14, the control circuitry configured to:
    enable a continuation of the level of user interaction using a vehicle system, while the operation of the user device is restricted.

16. The system of claim 14, the control circuitry configured to:
    determine a level of autonomy of the vehicle, wherein the interaction value is based on the level of autonomy of the vehicle.

17. The system of claim 10, the control circuitry configured to:
    determine a physiological parameter of the user; and
    estimate the level of tension of the user based on the physiological parameter.

18. The system of claim 10, wherein determining the range of permitted orientations comprises:
    determining a datum position of the user's head relative to the user device; and
    determining, relative to the datum, a range of permitted movement around or along at least one degree of movement of the user's head.

* * * * *